(12) United States Patent
Vrba

(10) Patent No.: US 6,168,621 B1
(45) Date of Patent: *Jan. 2, 2001

(54) BALLOON EXPANDABLE STENT WITH A SELF-EXPANDING PORTION

(75) Inventor: Anthony C. Vrba, Maple Grove, MN (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/087,526

(22) Filed: May 29, 1998

(51) Int. Cl.[7] .................................................. A61F 2/06
(52) U.S. Cl. ............................. 623/1.2; 623/1.3; 623/1.15
(58) Field of Search ............................... 623/1, 12, 1.25, 623/1.31, 1.3, 1.35, 1.2, 1.15; 606/198

(56) References Cited

U.S. PATENT DOCUMENTS

| 5,226,913 | * | 7/1993 | Pinchuk | 623/1 |
| 5,383,892 | * | 1/1995 | Cardon et al. | 606/198 |
| 5,607,444 | * | 3/1997 | Lam | 606/194 |
| 5,632,762 | | 5/1997 | Myler . | |
| 5,639,278 | * | 6/1997 | Dereume et al. | 623/1 |
| 5,643,312 | * | 7/1997 | Fishell et al. | 606/198 |
| 5,723,003 | * | 3/1998 | Winston et al. | 623/1 |
| 5,749,890 | | 5/1998 | Shaknovich . | |
| 5,776,162 | | 7/1998 | Kleshinski . | |
| 5,868,783 | * | 2/1999 | Tower | 606/198 |
| 5,879,370 | * | 3/1999 | Fischell et al. | 606/198 |
| 5,906,640 | * | 5/1999 | Penn et al. | 623/1 |

FOREIGN PATENT DOCUMENTS

WO 98/19628   5/1998   (WO) .

* cited by examiner

Primary Examiner—David H. Willse
Assistant Examiner—Suzette Jackson
(74) Attorney, Agent, or Firm—Vidas, Arrett & Steinkraus

(57) ABSTRACT

A stent consisting of at least two parts in juxtaposition, one part being of self-expandable characteristics while the other part is balloon expandable.

14 Claims, 4 Drawing Sheets

BALLOON EXPANDABLE STENT WITH A SELF-EXPANDING PORTION

FIELD OF THE INVENTION

The present invention relates to a new type of stent for transluminal implantation and in particular new vascular stents.

BACKGROUND OF THE INVENTION

Stents for transluminal implantation are well known. They are generally comprised of metallic supports which are inserted into a part of the human body such as bile ducts, the urinary system, the digestive tube and notably by percutaneous route inside the blood vessels, usually the arteries in which case they are typically termed vascular stents. Stents are usually generally cylindrical and are constructed and arranged to expand radially once in position within the body. They are usually inserted while they have a first relatively small diameter and implanted in a desired area, for example inside a vessel, then the stent is expanded in situ until it reaches a second diameter larger than the first diameter. A balloon associated with the catheter is usually used to provide the necessary interior radial force to the stent to cause it to expand radially. Self-expanding stents are also known which can expand from a first diameter to a larger second diameter without the use of a means for applying an interior radial force, such as a balloon, to them. One such type of self-expanding stent is a stent made of a shape memory metal which expands to its second larger diameter upon exposure to body temperature. Such stents are also known.

SUMMARY OF THE INVENTION

The present invention proposes a novel type of stent which combines a self-expanding part or portion with a part or portion which requires an interior radial force for expansion. More specifically, a stent for transluminal implantation according to the present invention will comprise cylindrical parts preferably in juxtaposition, with at least one part being self-expanding whereas another part requires an interior radial force for its expansion, such as a balloon catheter or the like. Basically, the stent will consist of at least two of the aforementioned parts but may consist of more than two parts. Such an arrangement enables improved placement of the stent by providing immediate expansion in part upon release of the stent from its delivery catheter.

DETAILED DESCRIPTION OF THE PREFERRED EMBODIMENTS

Figure 1:
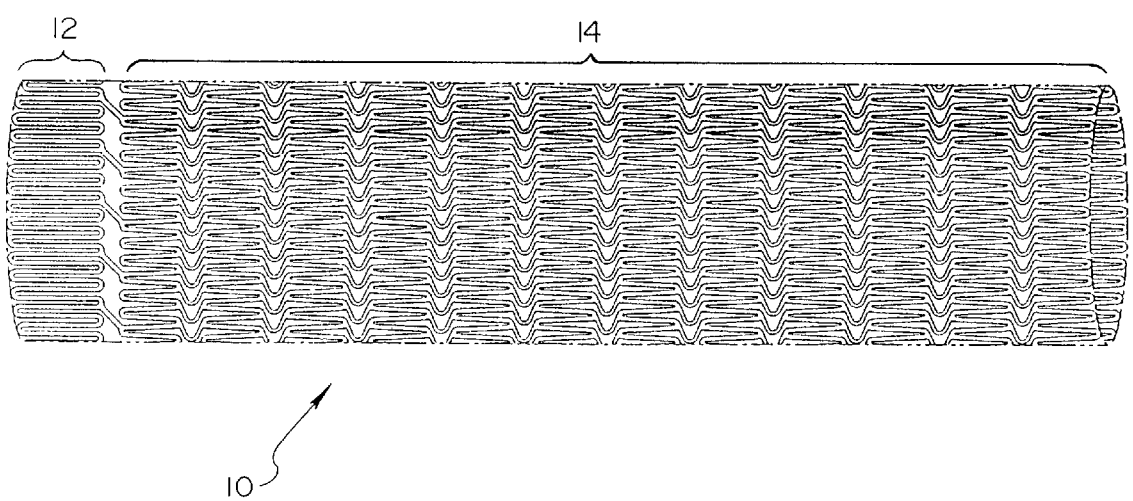
FIG. 1 is a showing of one embodiment of a stent according to this invention.

FIG. 1 shows a stent which combines self-expanding characteristics and balloon expandable characteristics, i.e., requires expansion by use of a radial interior force. Preferably, the stent will have the self-expanding part 12 joined at one end in juxtaposition to the proximal end of a balloon expandable stent 14. The parts of the stent may be formed in accordance with any of the known stents extant in the prior art. Preferably however, the self-expanding part 12 will be of a shape memory metal such as nitinol so as to enable self-expansion at body temperature upon release of the stent from its delivery catheter (not shown). The immediate expansion of part 12 aids in placement of the stent during release, following which a balloon or the like may be used to expand part 14.

Figure 2:
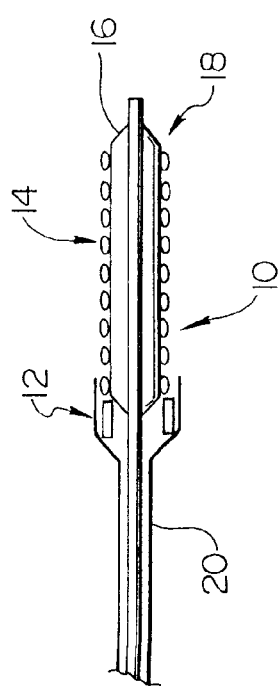
FIG. 2 is a schematic showing of a stent similar to that of FIG. 1 on a delivery catheter.
Figure 3:
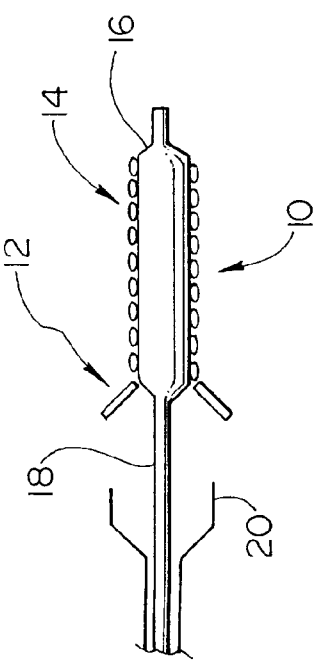
FIG. 3 is a schematic showing of the delivery system of FIG. 2 with the stent released for implantation.

Part 12 may be of a larger diameter, or it may be flared to provide the earliest possible contact with the body portion into which it is inserted, such as a vessel. This is best seen for example in FIGS. 2 and 3 which show a stent 10 similar to that of FIG. 1 on a delivery catheter. FIG. 2 shows the stent having the two parts 12 and 14, respectively. Part 12 is the self-expanding part while part 14 requires a separate force for expansion such as a balloon 16 of a delivery catheter generally indicated at 18 inside the stent. In FIG. 2, the stent is shown prior to release or deployment, the self-expanding part is enclosed by a retractable sheath 20. In FIG. 3, the sheath has been retracted, allowing self-expanding part 12 to flare-outwardly. Subsequently, balloon 16 may be used in the known manner to expand part 14.

Since most stent delivery catheters include a retractable sheath which exposes the stent for implantation and removal from the catheter, if the self-expanding part 12 is placed on the proximal end of the stent as shown, it will most likely be able to lock the stent in place until the remainder of the stent is expanded as by balloon expansion. This placement is preferable although placement in other parts of the stent proper may also be used.

Figure 4:
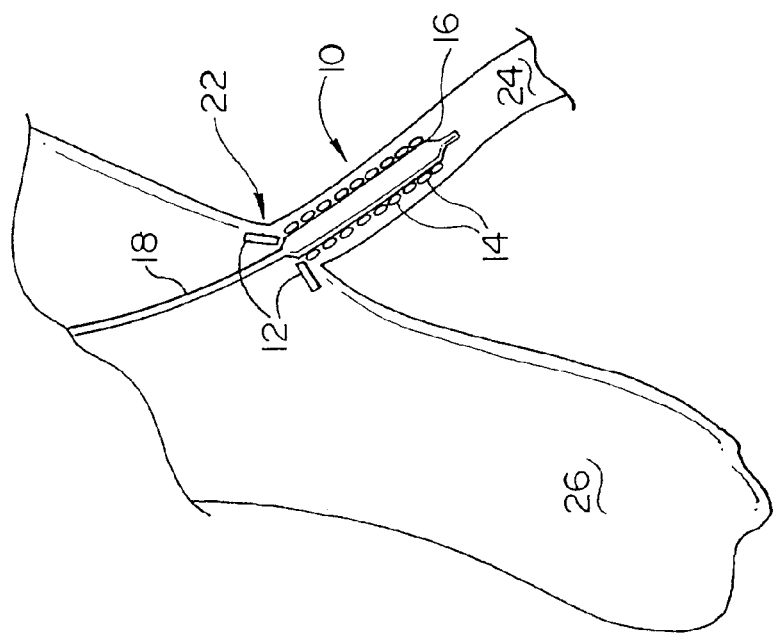
FIGS. 4 and 5 are schematic showings of a stent of the invention used in a vessel branching situation.
Figure 5:
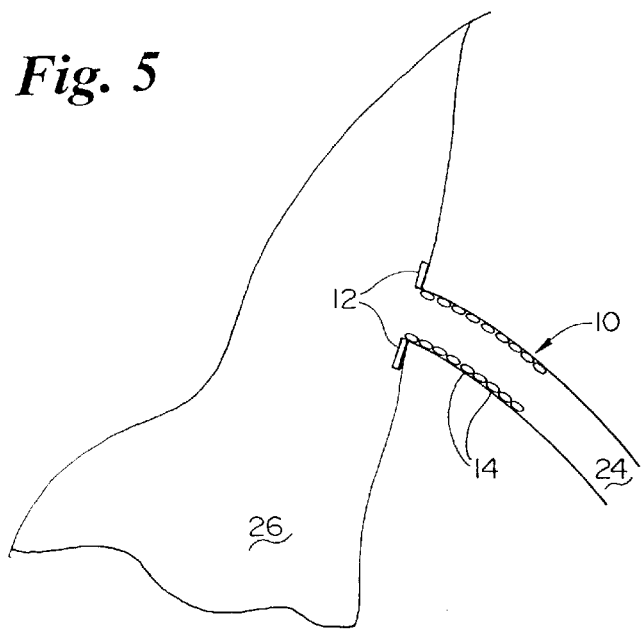

When the self-expanding portion is placed at the proximal end of the stent, such a stent is particularly useful in vessel stenting in which the vessel is of the bifurcating or branching type. Such a stent is shown schematically in FIGS. 4 and 5 at 10. FIG. 4 shows the stent having a proximal end part 12 which is self-expanding while the remainder of the stent body 14 is balloon expandable by balloon 16 on catheter 18. In FIG. 4, the retractable sheath has been removed allowing the self-expanding part to expand at the ostium 22 in a vessel 24 branching off of a main vessel such as aorta 26, helping to more accurately place the stent. FIG. 5 shows the stent after expansion of part 14 by the balloon catheter and catheter retraction. A stent according to the present invention allows positive placement of the stent near the ostium of the bifurcation.

Figure 6:
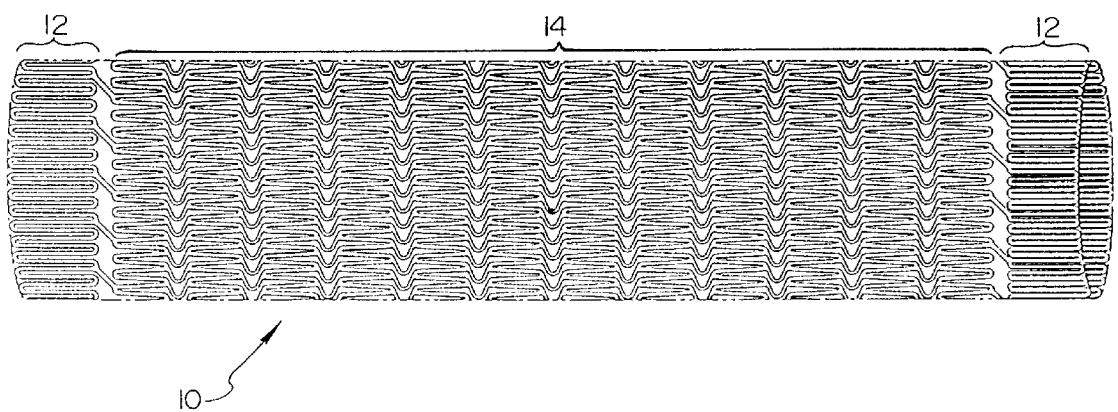
FIG. 6 is a showing of another embodiment of a stent according to the invention.

Stents according to the invention may also be comprised of more than one self-expanding and one balloon expandable part. Any combination of these parts is deemed to be within the scope of this invention. For example, referring to FIG. 6, a stent 10 is shown having a self-expanding part 12 at each end of a balloon expandable part 14.

Figure 7:
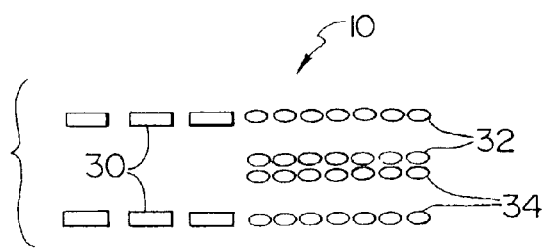
FIGS. 7–10 are schematic showings of bifurcated stents making use of the invention.

Referring now to FIGS. 7–10, bifurcated stents making use of the invention are described. Generally, bifurcated stents consist of three segments or components, a main trunk and two branches. In making use of this invention, any of the three components may be made to be balloon expandable or self-expandable, as desired. For example, FIG. 7 shows an unexpanded bifurcated stent 10 of one configuration in schematic form having a trunk 30, a first branch 32 and a second branch 34. As shown, trunk 30 is self-expanding, such as part 12 in the earlier Figures, and branches 32 and 34 are balloon expandable, such as part 14 in the earlier Figures.

Figure 8:
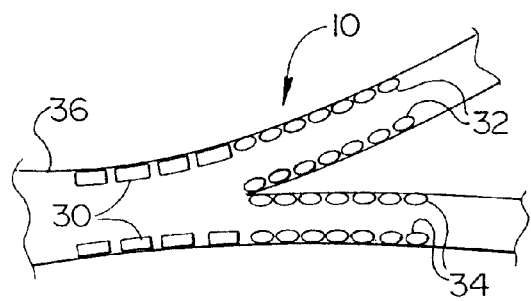

FIG. 8 shows the stent of FIG. 7 in an implanted position in a branching vessel 36.

Figure 9:
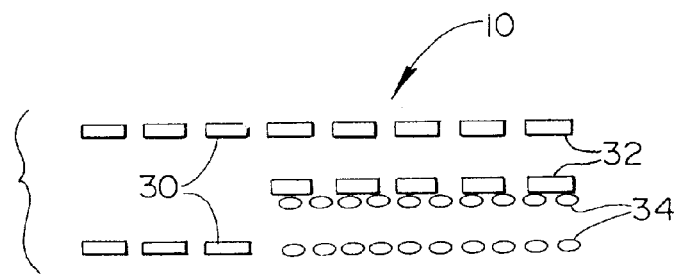

FIG. 9 shows another example of an unexpanded bifurcated stent 10 of another configuration in schematic form consisting of trunk 30 and branches 32 and 34. In this case, trunk 30 and branch 23 are both self-expanding and branch 34 is balloon expandable.

Figure 10:
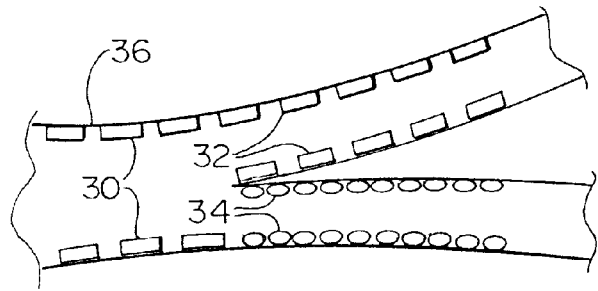

FIG. 10 shows the stent of FIG. 9 expanded in an implanted position in a branching vessel 36.

Trunk 30 in another embodiment may be balloon expandable while the branches 32 and 34 may be self-expandable.

The above Examples and disclosure are intended to be illustrative and not exhaustive. These examples and description will suggest many variations and alternatives to one of ordinary skill in this art. All these alternative, and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent for transluminal implantation comprised of a trunk and at least two joined cylindrical parts extending from the trunk, one part being capable of radially self-expanding, the other part being radially expandable only by means of a force applied thereto.

2. The stent of claim 1 wherein the two parts are in juxtaposition.

3. The stent of claim 1 wherein the other part is balloon expandable.

4. The stent of claim 1 wherein the one part is comprised of nitinol.

5. The stent of claim 1 wherein the one part comprises a proximal portion of the stent.

6. A stent for transluminal implantation comprised of a trunk and at least two joined cylindrical parts extending from the trunk, one part being capable of radially self-expanding, the other part being radially expandable only by means of an interior radial force wherein the one part comprises a proximal portion of the stent and wherein the one part is flared with respect to the rest of the stent when in the expanded condition.

7. The stent of claim 1 wherein the trunk further comprises a first end and a second end, the one part extending from the first end, the other part extending from the second end.

8. The stent of claim 1 wherein the trunk is balloon expandable.

9. The stent of claim 1 wherein the trunk is self-expandable.

10. The stent of claim 1 wherein the one part comprises a first undulating band having alternating peaks and troughs, the first undulating band comprising interconnected struts of a first length and the other part comprises a second undulating band having alternating peaks and troughs, the second undulating band comprising interconnected struts of a second length, the first length greater than the second length.

11. An expandable bifurcated stent comprising a trunk, a first branch and a second branch, the first branch and the second branch each extending from the trunk, the stent comprising a self-expanding portion and a portion which requires the application of a force thereto to expand wherein the self-expanding portion comprises at least one of the trunk, the first branch and the second branch, and the portion which requires the application of a force thereto to expand comprises at least one of the trunk, the first branch and the second branch.

12. The stent of claim 11 wherein the portion which requires the application of a force thereto to expand comprises a plurality of interconnected undulating bands having alternating peaks and troughs, and a plurality of curved interconnecting elements extending between adjacent bands.

13. The stent of claim 12 wherein the curved interconnecting elements are substantially U-shaped.

14. The stent of claim 11, the portion which requires the application of a force thereto to expand comprising a first undulating band having alternating peaks and troughs, and the portion which requires the application of a force thereto to expand comprising a second undulating band having alternating peaks and troughs, wherein the portion which self expands is connected to the portion which requires the application of a force thereto by interconnecting elements, each interconnecting element extending from a peak on a first undulating band to a trough on a second undulating band.

* * * * *